(12) United States Patent
Yeh et al.

(10) Patent No.: US 11,103,167 B2
(45) Date of Patent: Aug. 31, 2021

(54) SYSTEMS AND METHODS FOR SELF-EMISSION GLUCOSE MONITORING USING A GUIDED-MODE RESONANCE FILTER ARRAY

(71) Applicants: Yen-Chun Yeh, Menlo Park, CA (US); Sheng Yang, San Francisco, CA (US); Dominik J. Schmidt, Los Altos, CA (US)

(72) Inventors: Yen-Chun Yeh, Menlo Park, CA (US); Sheng Yang, San Francisco, CA (US); Dominik J. Schmidt, Los Altos, CA (US)

( * ) Notice: Subject to any disclaimer, the term of this patent is extended or adjusted under 35 U.S.C. 154(b) by 210 days.

(21) Appl. No.: 15/890,179

(22) Filed: Feb. 6, 2018

(65) Prior Publication Data

US 2018/0228410 A1 Aug. 16, 2018

Related U.S. Application Data

(60) Provisional application No. 62/457,633, filed on Feb. 10, 2017.

(51) Int. Cl.
*A61B 5/1455* (2006.01)
*G02B 5/18* (2006.01)
(Continued)

(52) U.S. Cl.
CPC .......... *A61B 5/1455* (2013.01); *A61B 5/0075* (2013.01); *A61B 5/14532* (2013.01);
(Continued)

(58) Field of Classification Search
None
See application file for complete search history.

(56) References Cited

U.S. PATENT DOCUMENTS

2013/0130939 A1* 5/2013 Wawro ................. G01N 21/253
506/18

OTHER PUBLICATIONS

Yeh et al.,"Self-emission glucose monitoring system with single chip guided-mode resonance filters," In Optical Diagnostics and Sensing XVI: Toward Point-of-Care Diagnostics, Proceedings of a meeting held Feb. 15-16, 2016. (5 pgs).

(Continued)

*Primary Examiner* — Eric F Winakur
*Assistant Examiner* — Marjan Fardanesh
(74) *Attorney, Agent, or Firm* — Strong & Hanni, P.C.; Joseph Shapiro

(57) ABSTRACT

Presented are systems and methods that perform noninvasive glucose monitoring using mid-infrared self-emission of the human body that acts as a background radiation emitter. Various embodiments accomplish this by taking advantage of the guided-mode resonance (GMR) effect in a number of bandpass filters that are constructed as an array of coplanar filters. The filter array acts as a spectral separator that uses a grating layer and a thin film waveguide to form reflection and transmission filters for particular wavelengths. Unlike, common multi-layer optical filter designs that utilize numerous individual optical filters, a novel GMR filter design comprises an array of filters that may be fabricated from CMOS-compatible materials using only a few thin film and grating layers to filter light. Advantageously, this reduces manufacturing cost and allows for simultaneous monitoring of a number of wavelengths of the glucose spectrum.

17 Claims, 7 Drawing Sheets

(51) Int. Cl.
| | |
|---|---|
| G02B 5/20 | (2006.01) |
| A61B 5/145 | (2006.01) |
| G01N 21/3577 | (2014.01) |
| G02B 6/34 | (2006.01) |
| G02B 6/12 | (2006.01) |
| G02B 6/132 | (2006.01) |
| A61B 5/00 | (2006.01) |
| G01N 21/35 | (2014.01) |

(52) U.S. Cl.
CPC ....... *G01N 21/3577* (2013.01); *G02B 5/1857* (2013.01); *G02B 5/208* (2013.01); *G02B 6/12002* (2013.01); *G02B 6/12004* (2013.01); *G02B 6/132* (2013.01); *G02B 6/34* (2013.01); *A61B 5/7257* (2013.01); *A61B 2562/0242* (2013.01); *G01N 2021/3595* (2013.01); *G02B 2006/12109* (2013.01)

(56) References Cited

OTHER PUBLICATIONS

Nelson et al.,"Development and validation of a multiwavelength spatial domain near-infrared oximeter to detect cerebral hypoxia-ischemia," Journal of Biomedical Optics 11(6), 2006. (8 pgs).
Shen et al.,"The use of Fournier-transform infrared spectroscopy for the quantitative determination of glucose concentration in whole blood," Phys Med Biol, Paper 48, 2023-2032, 2003. (3 pgs).
Enejder et al.,"Raman spectroscopy for non-invasive glucose measurements," Journal of Biomedical Optics, Paper 10, 031114, 2005. (9 pgs).
Malchoff et al.,"A novel noninvasive blood glucose monitor," Diabetes Care, Paper 25, 2668-2275, 2002. (9 pgs).
Wang et al.,"Theory and application of guided mode resonance filters," Appl. Phys. Lett, Papers 32, 2606-2613, 1993. (1 pg).
Shin et al.,"Thin-film optical filters with diffractive elements and waveguides," Opt. Eng., Paper 37(9), 2634-2646, 1998. (5 pgs).
Magnusson & Wang,"New principles for optical filters," Appl. Phys. Lett, Papers 61, 1022-1024, 1992. (4 pgs).
Vonach et al.,"Application of mid-infrared transmission spectrometry to the direct determination of glucose in whole blood," Applied Spectroscopy, Paper 52, 820-822,1998. 2pgs.
Planck et al.,"The Theory of Heat Radiation," Dover Publications, New York (1914). [online], [Retrieved Nov. 6, 2019]. Retrieved from Internet <URL: https://www.gutenberg.org/files/40030/40030-pdf.pdf> (14pgs).
Election/Restriction Requirement dated Oct. 8, 2019, in related U.S. Appl. No. 15/890,206. (6 pgs).
Resposonse filed Nov. 6, 2019, in related U.S. Appl. No. 15/890,206. (6 pgs).
Yanga et al.,"Single chip AWG-based Raman spectroscopy for continuous glucose monitoring," In Optical Diagnostics and Sensing XVI: Toward Point-of-Care Diagnostics, Proceedings of a meeting held Feb. 15-16, 2016. (6 pgs).
Zhang et al.,"Global healthcare expenditure on diabetes for 2010 and 2030," Diabetes Res Clin Pract. Papers 87(3), 293-301, 2010. (2 pgs).
Kurnik et al.,"Application of the Mixtures of Experts algorithm for signal processing in a noninvasive glucose monitoring system," Sensors and Actuators B: Chemical. Papers 60(1), 19-26,1999. (2 pgs).
Lee et al.,"Glucose measurements with sensors and ultrasound," Ultrasound Med Biol. Papers 31(7), 971-977 , 2005. (2 pgs).
Schrader et al."Non-invasive glucose determination in the human eye," J. Mol. Struct. Papers 735-736, 299-306, 2005. (2 pgs).
Martin et al.,"Using two discrete frequencies within the middle infrared to quantitatively determine glucose in serum," J. Biomed. Opt. Papers 7(4), 613-617, 2002. (1 pg).
Chaiken et al.,"Effect of hemoglobin concentration variation on the accuracy & precision of glucose analysis using tissue modulated, noninvasive, in vivo Raman spectroscopy of human blood: a small clinical study," J. Biomed. Opt. Papers 10(3), 031111 , 2005. (2 pgs).
Vashist et al.,"Non-invasive glucose monitoring technology in diabetes management: A review," Anal. Chim. Acta. Papers 750, 16-27, 2012. (1 pg).
Lyandres et al.,"Progress Toward an In Vivo Surface-Enhanced Raman Spectroscopy Glucose Sensor," Diabetes. Technol. Ther. Papers 10(4), 257-265, 2008. (18 pgs).
Berger et al.,"Multicomponent blood analysis by nearinfrared Raman spectroscopy," Appl. Opt. Papers 38(13), 2916-2926, 1999. (11 pgs).
Ismail et al.,"Raman spectroscopy with an integrated arrayed-waveguide grating," Opt. Lett. Papers 36(23), 4629-4631, 2011. (4 pgs).

\* cited by examiner

500

600

650

700

SYSTEMS AND METHODS FOR SELF-EMISSION GLUCOSE MONITORING USING A GUIDED-MODE RESONANCE FILTER ARRAY

CROSS REFERENCE TO RELATED PATENT APPLICATIONS

The present application claims priority to U.S. Provisional Application Ser. No. 62/457,633, titled "Systems and Methods for Self-Emission Glucose Monitoring Using a Guided-Mode Resonance Filter Array," filed on Feb. 10, 2017 and naming as inventors, Yen-Chun Yeh, Sheng Yang, and Dominik J. Schmidt, which application is incorporated herein by reference as to its entire content.

BACKGROUND

A. Technical Field

The present disclosure relates to diagnostic sensor systems. More particularly, the present disclosure related to systems and methods for monitoring chemicals, such as blood glucose levels, by using optical devices.

B. Description of the Related Art

One of the important aspects of diabetes treatment is the monitoring of blood glucose levels to help diabetes patients with diet control, oral medication, and insulin injection. Traditionally, diabetes patients have to use a lancet to puncture their finger to extract a drop of blood that is collected on a disposable test strip and inserted into a blood glucose measurement device that performs a chemical analysis to determine the patient's current blood glucose level. However, this method unnecessarily inflicts pain on the patient, and requires disposable test strips that incur continuous expenses. The desire to make blood glucose monitoring a painless and affordable process spurred research of non-invasive glucose sensing techniques.

Current non-invasive glucose monitoring techniques that utilize optical methods include near-infrared (NIR) spectroscopy, mid-infrared (MIR) spectroscopy, and Raman spectroscopy. Only one of these methods, MIR spectroscopy, is capable of measuring glucose without requiring an external light source, namely, by utilizing the human body's own emissions in the MIR spectrum. However, non-invasive glucose monitoring using MIR spectroscopy has its own drawbacks as it requires that at least two different wavelengths in the MIR range be measured to obtain a glucose characteristic peak and a reference peak. Additional requirements include the use of a dual channel thermometer and two rather expensive optical bandpass filters.

What is needed are non-invasive optical monitoring systems and methods that overcome the limitations of existing approaches and that provide low-cost solutions for diabetes patients.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

Figure 1:
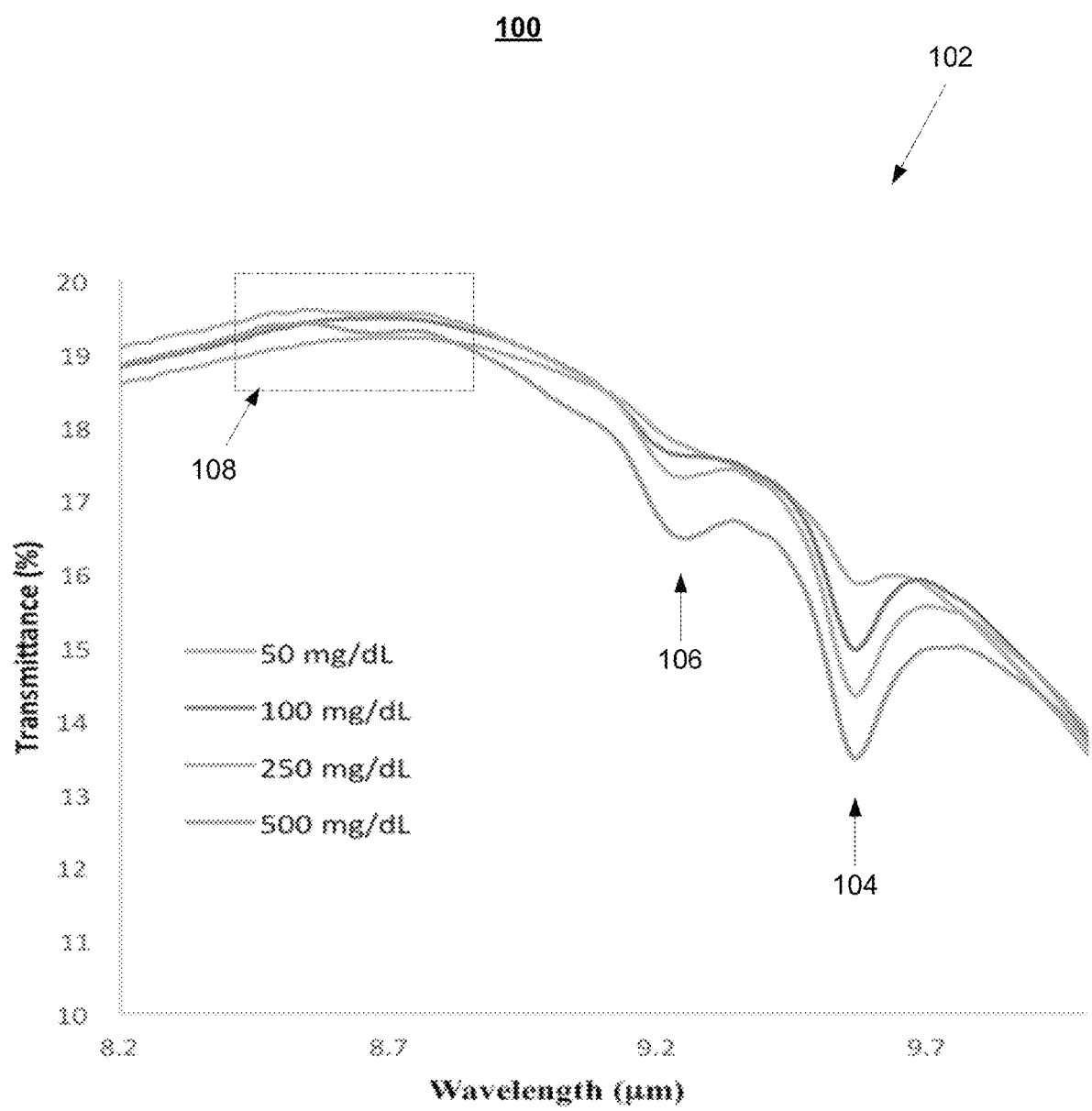
FIG. 1 shows measurement results of a Fourier transform infrared (FT-IR) spectroscopy for a transmission spectrum of glucose in deionized water in a BaF2 liquid cell according to various embodiments of the present disclosure.

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled," "connected," or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated. Furthermore, the use of memory, database, information base, data store, tables, hardware, and the like may be used herein to refer to system component or components into which information may be entered or otherwise recorded.

Furthermore, it shall be noted that: (1) certain steps may optionally be performed; (2) steps may not be limited to the specific order set forth herein; (3) certain steps may be performed in different orders; and (4) certain steps may be done concurrently.

The presence of glucose molecules in the human body causes certain distinct peaks to appear in the mid-infrared spectrum, which allows for the estimation of a glucose concentration based on the peak intensity within the spectrum. Since the human body can be viewed as a good blackbody radiator that provides stable temperature and continuous radiation in the mid-infrared range, various embodiments of the present disclosure treat the body as a radiation source and measure a corresponding emission spectrum to determine a blood glucose concentration.

FIG. 1 shows measurement results of a Fourier transform infrared (FT-IR) spectroscopy for a transmission spectrum of glucose in deionized water in a BaF2 liquid cell according to various embodiments of the present disclosure. In embodiments, liquid samples of different glucose concentrations may be diluted from 45% D-(+)-Glucose solution. As shown in FIG. 1, transmission spectra 102 for liquid glucose samples comprising 50 mg/dL, 100 mg/dL, 250 mg/dL, and 500 mg/dL exhibit a relatively strong glucose absorption peak 104 at a wavelength of about 9.56 µm and a weaker absorption peak 106 at a wavelength of about 9.25 µm. As the measurement results demonstrate, glucose absorption increases as glucose concentration is increased.

Since, in accordance with Plank's law, radiation intensity is very temperature sensitive in the mid-infrared region of the spectrum, in embodiments, quasi-isosbestic points 108 that are relatively insensitive to the glucose concentration may be used as temperature references to calibrate the glucose concentration. In embodiments, such glucose insensitive locations, i.e., wavelengths at which the transmittance remains relatively constant independent of the glucose concentration in the sample, are used at, e.g., 8.3 µm, 8.5 µm, and 9.9 µm.

Figure 2:
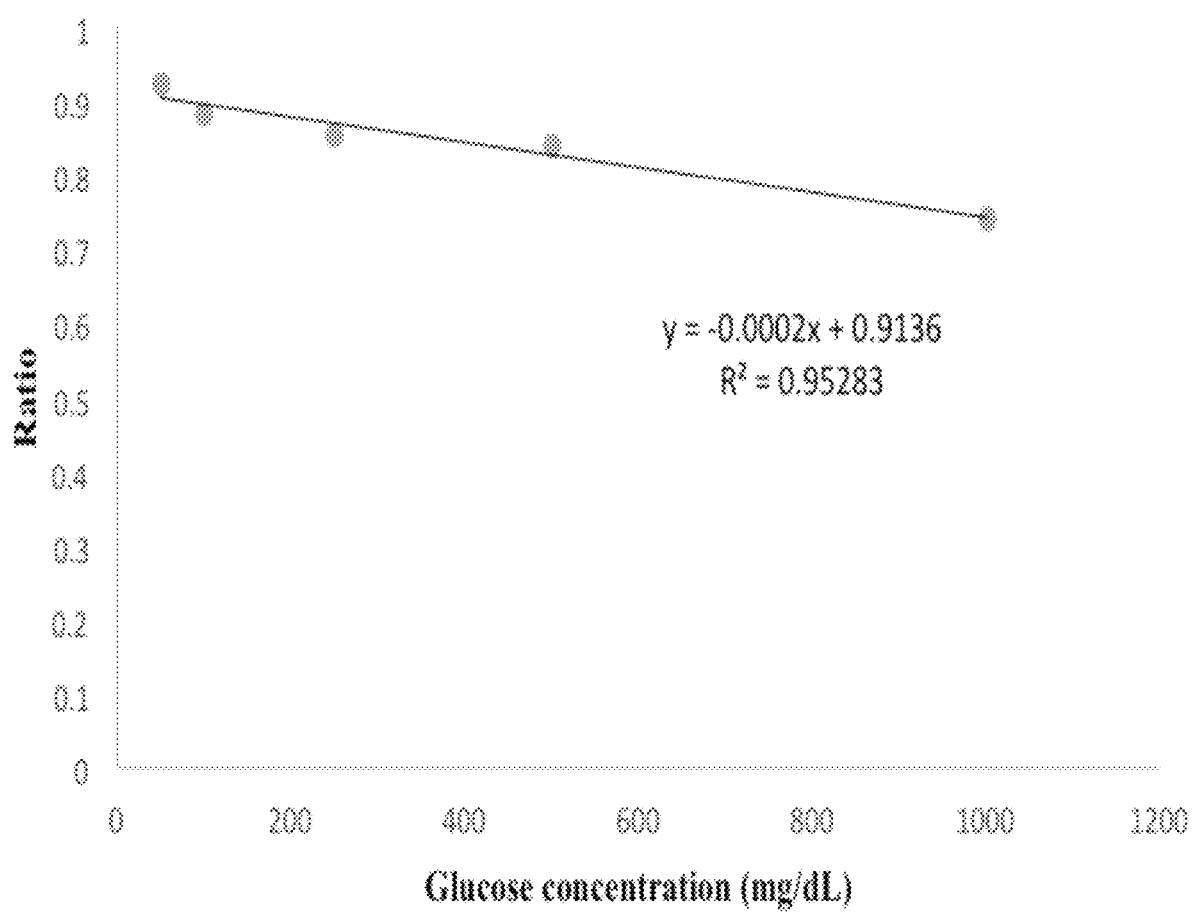
FIG. 2 shows measurement results of ratios of glucose sensitive peaks and to glucose insensitive peaks according to various embodiments of the present disclosure.

FIG. 2 shows measurement results of ratios of glucose sensitive peaks to glucose insensitive points according to various embodiments of the present disclosure. As shown, the $R^2$ correlation for the ratio of the transmission value for the glucose sensitive peak at a wavelength of 9.56 µm to the transmission value for the glucose insensitive value measured at 8.3 µm and 8.7 µm is 0.95. In embodiments, the results of FIG. 2 may be used to obtain a glucose concentration based on the measured ratio.

Since the human body contains many different chemicals that each has its unique spectrum and fingerprint peaks, some of these peaks may appear close to the glucose characteristic peaks region. Therefore, in embodiments, the intensity of two or more wavelengths within the glucose characteristic peaks region are measured and compensated for as part of a calibration that aids in reducing the error caused by unwanted characteristic peaks present in the bloodstream.

Figure 3A:
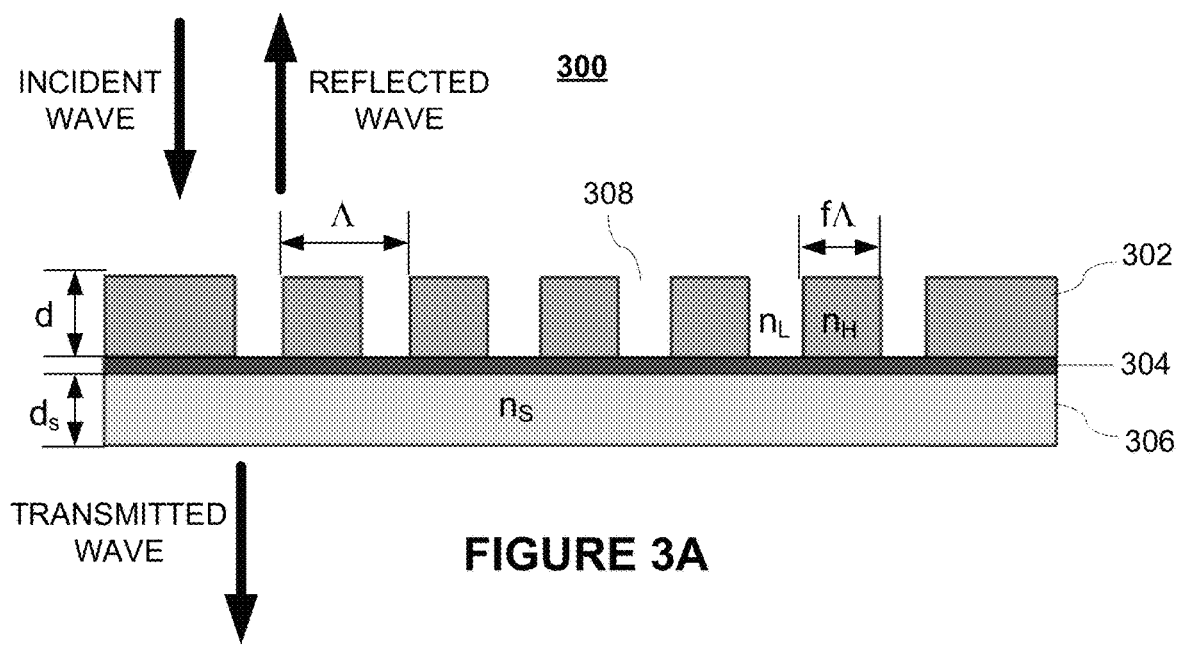
FIG. 3A illustrates an exemplary structural design of a single-layer guided-mode resonance (GMR) bandpass filter according to various embodiments of the present disclosure.

FIG. 3A illustrates an exemplary structural design of a single-layer GMR bandpass filter according to various embodiments of the present disclosure. GMR bandpass filter 300 comprises grating structure 302, etch stop layer 304, and substrate 306. In embodiments, grating structure 302 is formed next to etch stop layer 304 (e.g., TiO2) that is in contact with substrate 306. In embodiments, grating structure 302 is implemented as a germanium layer comprising trenches 308 that define a grating period (Λ) and a fill factor, f. In embodiments, substrate 306 is implemented as a silicon (e.g., amorphous silicon) layer that serves as a waveguide structure. As depicted, a wave that is incident on grating structure 302 is partially reflected and partially transmitted through GMR bandpass filter 300.

In FIG. 3A, $n_S$ and $n_H$ represent the respective refractive indices of the materials of two different layers 302 and 306 of GMR filter 300; $n_L$ is the refractive index of air; and d and $d_S$ are the respective thicknesses of the materials. In embodiments, the material of grating structure 302 has a thickness d of 4.18 µm and a refractive index of 4.0; the material of waveguide structure 306 has a thickness $d_s$ of 2.2 µm and a refractive index $n_S$ equal to 3.7; and $n_L$ is the refractive index of air present in trench 308.

In embodiments, the fill factor may be adjusted (e.g., to a value between 0.444 and 0.533) to compensate for a potential peak shift that may be caused by etch stop layer 304. It is understood that GMR filter 300 may be implemented as a reflection filter or a transmission filter. It is further understood that any dimensions and measurements herein are merely for purposes of illustration and not intended as a limitation on the scope of the present disclosure.

Figure 3B:
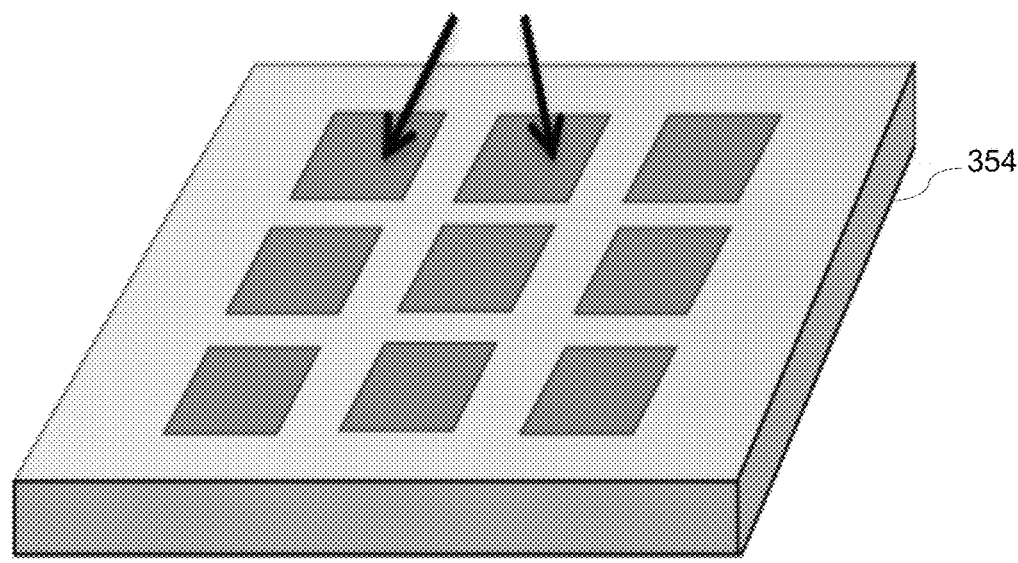
FIG. 3B illustrates an exemplary structural design of a single-layer GMR bandpass filter array according to various embodiments of the present disclosure.

FIG. 3B illustrates an exemplary structural design of a single-layer GMR bandpass filter array according to various embodiments of the present disclosure. GMR filter array 350 comprises any number of GMR filters 352 located on the same chip or die 354 comprising, e.g., a monolithic substrate. In embodiments, GMR filter array 350 comprises two or more different narrow bandpass filters. In embodiments, to produce different filters on chip 354, the grating period, Λ, and the fill factor, f, may be adjusted to obtain individual filter characteristics, while the thicknesses of the grating structure and the thicknesses of the substrate 354 may remain constant. As a result, two or more GMR filters 352 having different opto-electronical characteristics (e.g., different center frequencies and frequency responses) may be constructed on chip 354.

In embodiments, GMR filters 352 utilize the GMR effect in order to achieve optical glucose monitoring. In embodiments, GMR filter 350 array is combined with a detector array and a bandpass filter (not shown) to achieve non-invasive glucose monitoring. For example, such as an infrared detector that uses mercury cadmium telluride (HgCdTe) as detector material, may be located adjacent to each GMR filter 352 to receive and detect a mid-infrared signal within a glucose sensing device that comprises both GMR filter array 350 and the detector array.

Figure 6A:
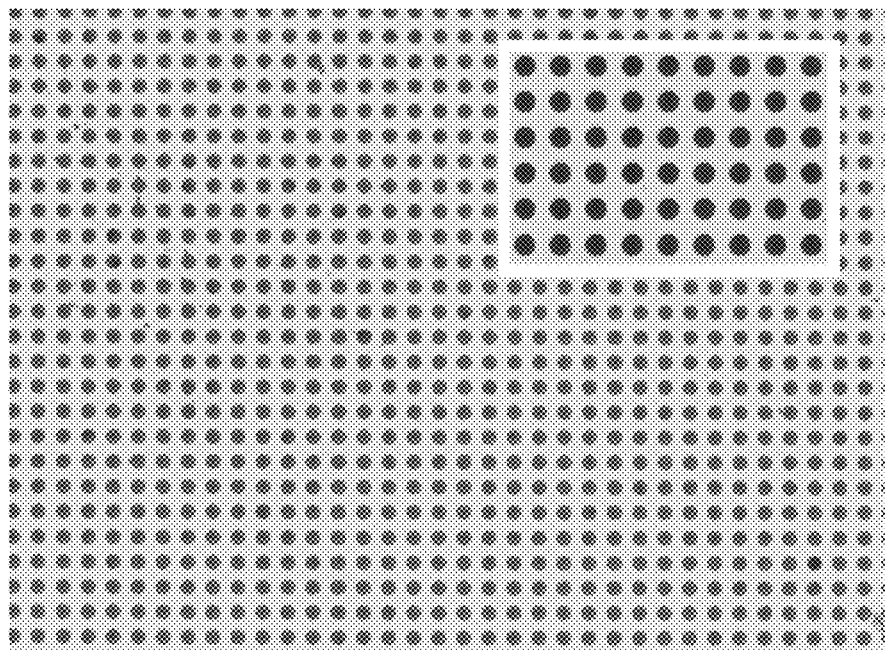
FIG. 6A illustrates a top view of an exemplary GMR filter array comprising GMR filters, according to various embodiments of the present disclosure.
Figure 6B:
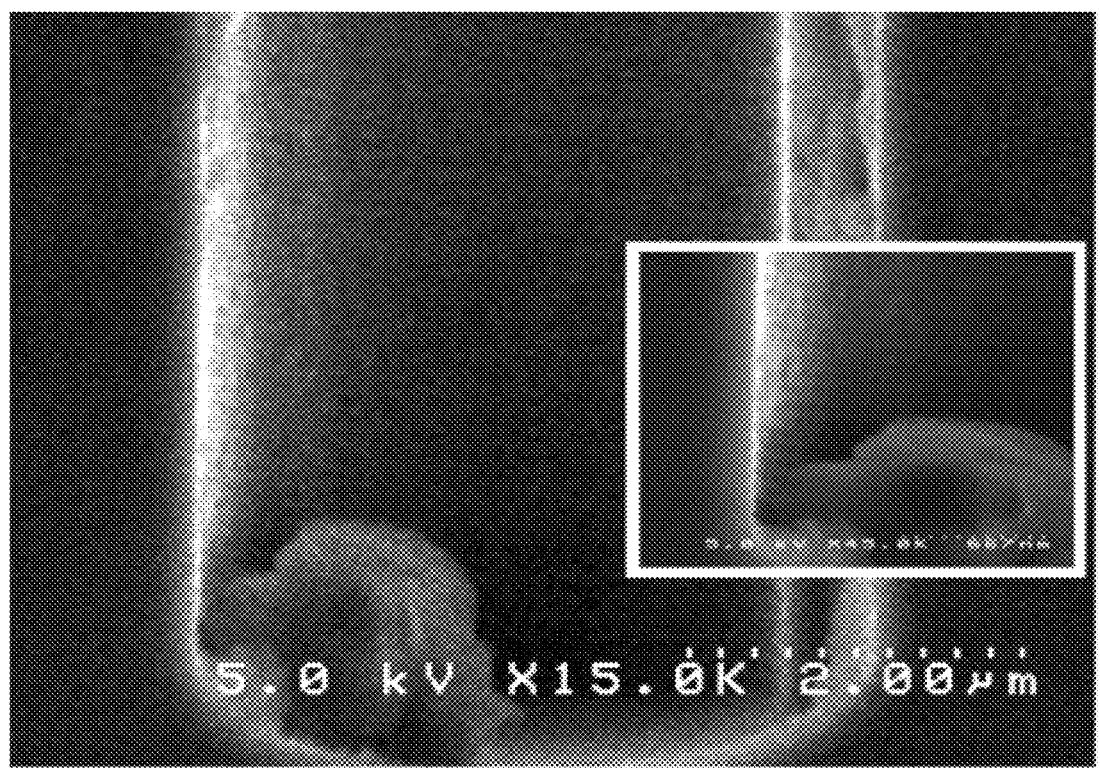
FIG. 6B is a SEM picture of a cross-section of a GMR filter shown in FIG. 6A.

FIG. 6A illustrates a top view of an exemplary GMR filter array comprising GMR filters, according to various embodiments of the present disclosure. As depicted, the GMR filter array has cylindrical features. However, this is not intended as a limitation on the scope of the invention as other feature geometries, such as hexagonal, are equally possible. FIG. 6B is a SEM picture of a cross-section of the GMR filter in FIG. 6A.

Figure 4:
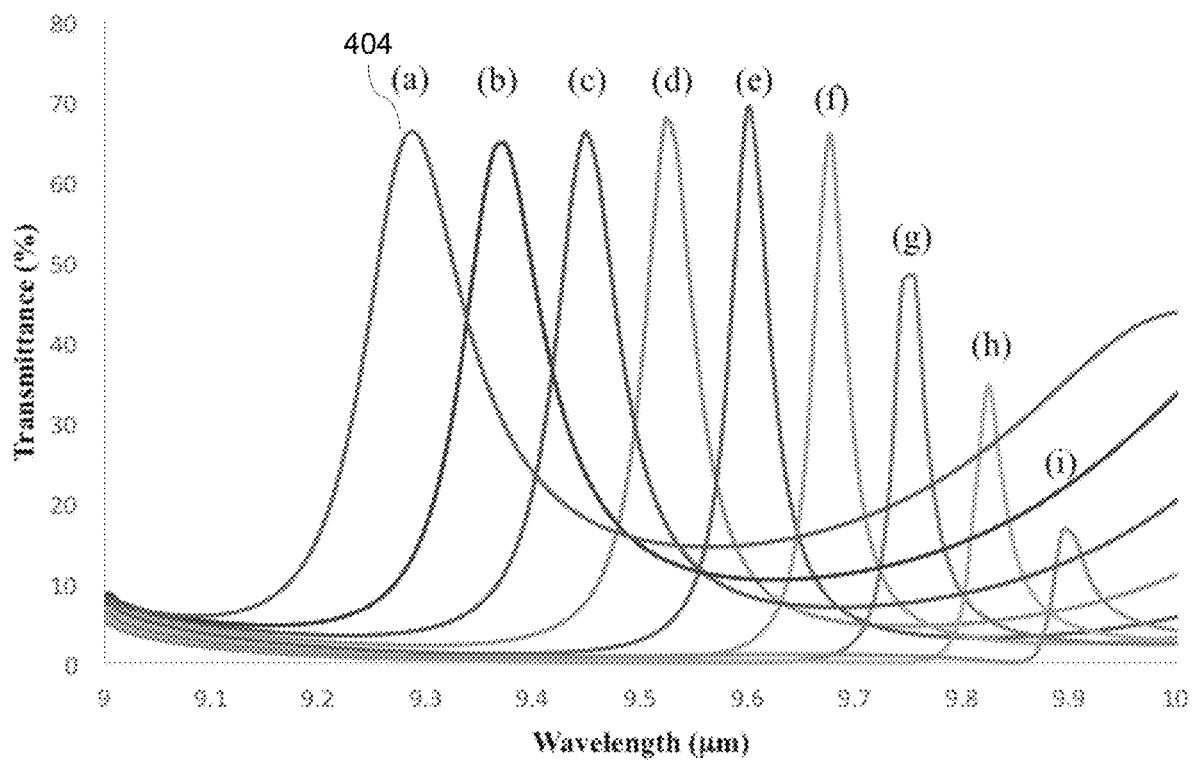
FIG. 4 is a plot illustrating simulation results for a spectral response of the GMR filter array shown in FIG. 3B.

FIG. 4 is a plot illustrating simulation results for a spectral response of the GMR filter array shown in FIG. 3. As shown in a COMSOL simulation 400 in FIG. 4, a series of transmittance peaks 404 of up to 70% and bandwidths of around 200 nm may be achieved. The simulation results for the TE mode depict several narrow linewidths within a range from 9 μm to 10 μm obtained for various combinations of values for Λ and f. In embodiments, the filters facilitate the separation of the glucose characteristic peaks from glucose insensitive regions. For graph (a), centered at 9.28 μm in FIG. 4, the grating period, Λ, is 9 μm, the fill factor, f, is =0.444, and the transmittance, T, is 66%; for graph (b), centered at 9.36 mm, Λ is 9 μm, f is 0.455, T is 64%; for graph (c), centered at 9.47 μm, Λ is 9 μm, f is 0.467, T is 66%; for graph (d), centered at 9.51 μm, Λ is 9 μm, f is 0.478, T is 68%; for graph (e), centered at 9.60 μm, Λ is 9 μm, f is 0.489, T is 69%; for graph (f), centered at 9.67 μm, Λ is 9 μm, f is 0.500, T is 66%; for graph (g), centered at 9.75 μm, Λ is 9 μm, f is 0.511, T is 47%; for graph (h), centered at 9.82 μm, Λ is 9 μm, f is 0.522, T is 34%; and for graph (i), centered at 9.89 μm, Λ is 9 μm, f is 0.533, and T is 16%. In embodiments, suitable detectors, e.g., infrared detectors, may be used to receive body emissions filtered by the individual filters of the GMR filter array. Based on the filtered data, a determination may then be made, e.g., regarding the glucose content of blood.

It is understood that, for a given chip design, any combination of values for Λ, f, and refractive indices may be selected to adjust the transmission and reflection characteristics of any number of individual filters of the GMR filter array, for example, to perform a desired calibration or compensation method.

FIG. 5A-5D illustrate a process for fabricating a set of GMR filters according to various embodiments of the present disclosure. The fabrication process may result in any desired number of coplanar filters being fabricated at the same time and on the same chip 500. The filter set may be fabricated with a relatively low number of layers which simplifies the typical semiconductor deposition process. In embodiments, chip 500 comprises materials that have relatively low extinction coefficients in the wavelength region of interest, e.g., to avoid radiation absorption.

Figure 5A:
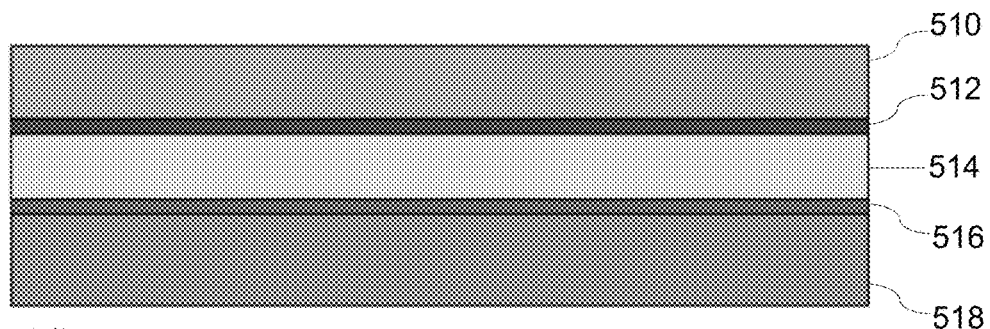
FIG. 5A-5D illustrate a process for fabricating a set of GMR filters according to various embodiments of the present disclosure.
Figure 5B:
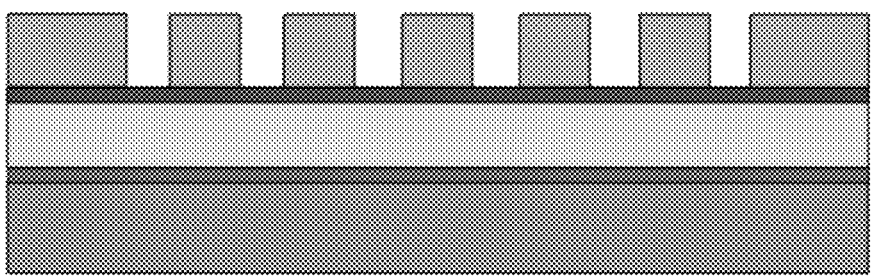
Figure 5C:
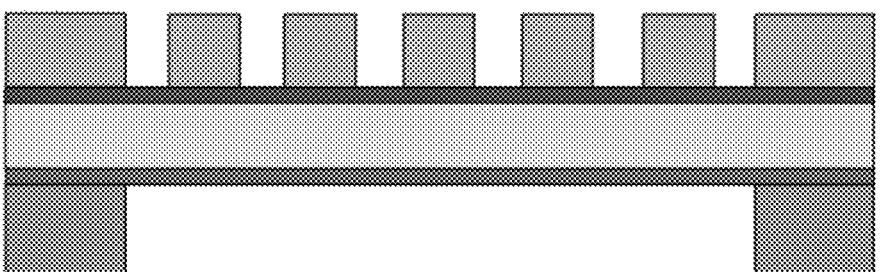
Figure 5D:
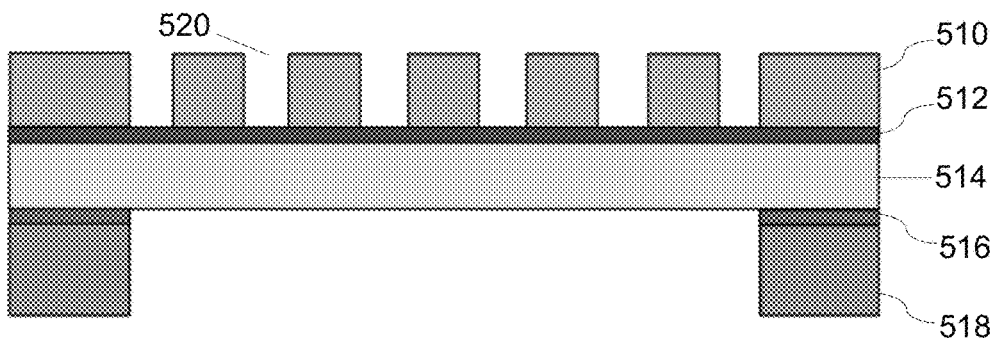

In embodiments, the fabrication process comprises depositing SiO$_2$, α-Si, TiO$_2$, and Ge on double polished wafer 518. As shown in FIG. 5D, Ge ($n_H$=4.0) deposition layer 510 may be used as grating thin film material, and α-Si ($n_s$=3.7) deposition layer 514 may be used as waveguide thin film material to form an optical waveguide. In embodiments, a 10 nm TiO$_2$ layer 512 may be used as etch stop layer that is in contact with both Ge layer 510 and α-Si layer 514.

Grating structure 520 may be patterned on Ge layer 510 using any photolithography method known in the art. In embodiments, Ge layer 510 is etched, e.g., by dry etch using a Bosch process, such as to leave TiO2 layer 512 as a stop layer that protects α-Si 514 from being etched away. In embodiments, SiO$_2$ layer 516 serves as a stop layer when etching away some or all of Si substrate 518 in the step shown in FIG. 5C.

In embodiments, the SiO$_2$ layer is partially or completely removed from the GMR structure, as shown in FIG. 5D, to reduce the effect that the extinction coefficient of SiO$_2$ may have on the working range and characteristic of the filter.

In embodiments, materials used to produce chip 500 are compatible with semiconductor CMOS fabrication processing, such that a plurality of GMR filters may be manufactured on a single-chip 500 to form a GMR filter array. Advantageously, this significantly reduces the cost of manufacturing when compared to today's commercially available discrete filter designs. In addition, replacing multiple individual bandpass filters with a single-chip filter set eliminates the need for multiple layers and thicknesses for each bandpass filter. In embodiments, a series of filters, e.g., an array of narrow bandpass filters that are designed to operate at a range between 9 μm and 10 μm, are formed on chip 500.

In embodiments, chip 500 may be embedded into a mid-infrared glucose sensing device that comprises one or more detectors, for example a sensitive integrated thermal detector array, may be placed adjacent to GMR chip 500 to measure glucose characteristic peaks in the emission spectrum of the human body and other peaks, e.g., to detect and compensate for the presence of unwanted molecules in a specific part of the spectrum.

Figure 7:
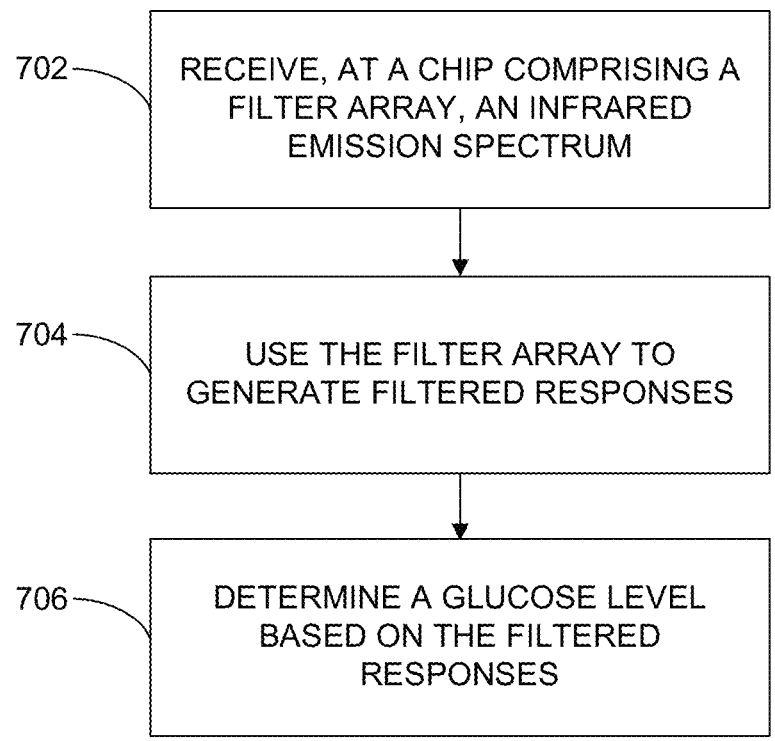
FIG. 7 is a flowchart of an illustrative process for monitoring blood glucose, in accordance with various embodiments of the present disclosure.

FIG. 7 is a flowchart of an illustrative process for monitoring blood glucose, in accordance with various embodiments of the present disclosure.

At step 702, an emission spectrum is received at a chip, e.g., a spectrum that comprises infrared radiation originating from a human body. The chip may comprise any number of optical and electrical components. In embodiments, the chip may comprise an array of filters, each filter being designed to filter some part of the emission spectrum. For example, each filter may utilize a GMR effect to reflect or transmit light at a certain range of wavelengths.

At step 704, the filter array is used to generate two or more filter responses associated with one or more parts of the received spectrum. It is noted that the filter array may comprise any type of filter or combination of filters. For example, two or more filters maybe used to generate one bandpass filter response.

At step 706, based on the filtered responses, a glucose level present in a human or animal body is determined, e.g., from a ratio of two of the filtered responses. In embodiments, one or more detectors may be placed adjacent to a filter in the array, such that each detector may detect a portion, e.g., a narrow and different portion, of the spectrum. This enables the detection of different bandpass characteristics using a single substrate. Since the GMR effect allows to control filter design by controlling the size and pitch of various openings using standard lithographic techniques, any arbitrary number of filters may be fabricated at a fixed cost.

In comparison, existing mid-infrared filters are fabricated using multiple deposition layers on a substrate. In addition, for each filter having a different passband characteristic, the entire fabrication process must be repeated, such that the manufacturing cost increases proportional to the number of individual filters.

One skilled in the art will recognize that a number of the elements described above may be physically and/or functionally separated into sub-modules or combined together. It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

What is claimed is:

1. A monolithic guided-mode resonance (GMR) filter array for noninvasive glucose monitoring, the filter array comprising:
   a grating that is defined by one or more grating periods and fill factors;

an optical waveguide located adjacent to the grating, the optical waveguide designed to carry light waves in one or more modes, the optical waveguide together with the grating forms two or more filters that operate at a range of wavelengths based on a GMR effect, the two or more filters being configured to filter an emission spectrum and generate a filtered response;

a substrate to support the grating and the optical waveguide;

one or more detectors configured to receive the filtered response to generate signals representative of glucose characteristic peaks; and a signal processing device that, in response to receiving the generated signals, determines a blood glucose level.

2. The filter array according to claim 1, wherein the grating, the optical waveguide, and the substrate are made using materials that are compatible with semiconductor fabrication processes.

3. The filter array according to claim 2, wherein the materials reduce radiation absorption by having a low extinction coefficient at the range of wavelengths.

4. The filter array according to claim 2, wherein the grating comprises trenches that are formed by a using and etch process.

5. The filter array according to claim 1, wherein the grating periods and fill factors are designed such that the two or more filters have different filter characteristics.

6. The filter array according to claim 1, wherein the grating comprises cylindrical features.

7. The filter array according to claim 1, wherein two or more filters comprise a bandpass filter that filters light in an infrared spectrum.

8. The filter array according to claim 1, wherein the range of wavelengths is from 8 μm to 11 μm inclusive.

9. The filter array according to claim 1, wherein the filter array is located on a semiconductor substrate.

10. The filter array according to claim 1, wherein the optical waveguide is designed to transmit lightwaves in a TE mode.

11. The filter array according to claim 1, wherein the grating is formed from a Germanium layer comprising trenches that define grating periods and fill factors, each grating period and fill factor being associated with at least one filter characteristic of the two or more filters.

12. A method for non-invasive blood glucose monitoring, the method comprising:

receiving, at a chip that comprises a filter array, an emission spectrum, the filter array comprising:
  a grating that is defined by one or more grating periods and fill factors;
  an optical waveguide located adjacent to the grating, the optical waveguide designed to carry light waves in one or more modes, the optical waveguide together with the grating forms two or more filters that operate at a range of wavelengths based on a GMR, effect, the two or more filters being configured to filter an emission spectrum and generate a filtered response;
  a substrate to support the grating and the optical waveguide;
  one or more detectors configured to receive the filtered response to generate signals representative of glucose characteristic peaks; and
  a signal processing device that, in response to receiving the generated signals, determines a blood glucose level;

using the one or more detectors to receive the filtered response to generate signals representative of glucose characteristic peaks; and using the signal processing device to, in response to receiving the generated signals, determine a glucose level.

13. The method according to claim 12, wherein the emission spectrum is received from a human body.

14. The method according to claim 12, wherein the filter array comprises a grating and an optical waveguide that form the two or more filters.

15. The method according to claim 12, wherein the two or more filters comprise bandpass filters that filter light in an infrared spectrum.

16. The method according to claim 15, further comprising receiving the filtered light at a detector to generate a signal representative of a glucose characteristic peak.

17. The method according to claim 16, further comprising determining a blood glucose level based on the signal.

* * * * *